US010975000B2

(12) United States Patent
Cadran et al.

(10) Patent No.: US 10,975,000 B2
(45) Date of Patent: Apr. 13, 2021

(54) STABILIZED PRODUCTION OF 1,3-BUTADIENE IN THE PRESENCE OF A TANTALUM OXIDE DOPED BY AN ALDOLIZING ELEMENT

(71) Applicants: IFP Energies Nouvelles, Rueil-Malmaison (FR); Compagnie Generale Des Etablissements Michelin, Clermont-Ferrand (FR)

(72) Inventors: Nicolas Cadran, Oullins (FR); Alexandra Chaumonnot, Lyons (FR)

(73) Assignees: IFP Energies Nouvelles, Rueil-Malmaison (FR); Compagnie Generale Des Etablissements Michelin, Clermont-Ferrand (FR)

( * ) Notice: Subject to any disclaimer, the term of this patent is extended or adjusted under 35 U.S.C. 154(b) by 139 days.

(21) Appl. No.: 15/744,266

(22) PCT Filed: Jul. 5, 2016

(86) PCT No.: PCT/EP2016/065822
§ 371 (c)(1),
(2) Date: Jan. 12, 2018

(87) PCT Pub. No.: WO2017/009106
PCT Pub. Date: Jan. 19, 2017

(65) Prior Publication Data
US 2018/0201553 A1 Jul. 19, 2018

(30) Foreign Application Priority Data

Jul. 13, 2015 (FR) ...................................... 15 56663

(51) Int. Cl.
| | | |
|---|---|---|
| *B01J 23/20* | (2006.01) | |
| *C07C 1/20* | (2006.01) | |
| *B01J 23/68* | (2006.01) | |
| *B01J 35/10* | (2006.01) | |
| *B01J 37/02* | (2006.01) | |

(52) U.S. Cl.
CPC ................ *C07C 1/20* (2013.01); *B01J 23/20* (2013.01); *B01J 23/682* (2013.01); *B01J 35/1019* (2013.01); *B01J 35/1023* (2013.01); *B01J 35/1038* (2013.01); *B01J 35/1042* (2013.01); *B01J 35/1047* (2013.01); *B01J 35/1061* (2013.01); *B01J 37/0201* (2013.01); *B01J 37/0203* (2013.01); *B01J 2523/00* (2013.01); *C07C 2521/10* (2013.01); *C07C 2523/02* (2013.01); *C07C 2523/06* (2013.01); *C07C 2523/14* (2013.01); *C07C 2523/20* (2013.01); *C07C 2523/68* (2013.01)

(58) Field of Classification Search
CPC . B01J 23/20; B01J 23/682; B01J 23/68; B01J 2523/00; B01J 2523/27; B01J 2523/57; B01J 2523/3712; B01J 2523/41; B01J 2523/18; B01J 2523/22; B01J 2523/3706; B01J 2523/02; B01J 35/1047; B01J 35/1019; B01J 35/1042; B01J 35/1061; B01J 35/1023; B01J 35/1038; C07C 11/167; C07C 2523/68; C07C 2523/20; C07C 2523/14; C07C 2523/06; C07C 2523/02
See application file for complete search history.

(56) References Cited

U.S. PATENT DOCUMENTS 3,895,049 A * 7/1975 Umemura ................ B01J 23/30
502/246

FOREIGN PATENT DOCUMENTS

| KR | 2014047329 A | 4/2014 | |
|---|---|---|---|
| KR | 20140050531 A | * 4/2014 | ............... C07C 1/20 |
| WO | 2013125389 A1 | 8/2013 | |

OTHER PUBLICATIONS

Corson, B. B. et. al. "Butadiene from ethyl alcohol", Industrial & Engineering Chemistry, (1950), 42, pp. 359-373. (Year: 1950).*
Chae, H-J. et. at. "Butadiene production from bioethanol and acetaldehyde over tantalum oxide-supported ordered mesoporous silica catalysts", Appl. Cat. B: Environmental, (2014), 150-151, pp. 596-604. (Year: 2014).*
Corson (NPL: "Butadiene from ethyl alcohol", Industrial & Engineering Chemistry, (1950), vol. 42, No. 2, pp. 359-373) (Year: 1950).*
Chae ("Butadiene production from bioethanol and acetaldehyde over tantalum oxide-supported ordered mesoporous silica catalyst", Appl. Cat. B: Environmental, (2014), 150-151, pp. 596-604). (Year: 2014).*
Kim (KR20140050531, machin translation) (Year: 2014).*
International Search Report PCT/EP2016/065822 dated Aug. 24, 2016.
B. B. Corson et al: "Butadiene from Ethyl Alcohol. Catalysis in the One-and Two-Stop Processes.", Industrial & Engineering Chemistry, vol. 42, No. 2, Feb. 1950 (Feb. 1, 1950), pp. 359-373, XP055051002, ISSN: 0019-7866.

* cited by examiner

*Primary Examiner* — Coris Fung
*Assistant Examiner* — Smita S Patel
(74) *Attorney, Agent, or Firm* — Millen, White, Zelano and Branigan, P.C.

(57) ABSTRACT

The invention relates to a catalyst that comprises at least the tantalum element, at least an aldolizing element and at least a mesoporous oxide matrix, with the tantalum mass being between 0.1 and 30% of the mesoporous oxide matrix mass, the mass of the at least one aldolizing element being between 0.02 and 4% of the mesoporous oxide matrix mass, and use thereof.

12 Claims, No Drawings

STABILIZED PRODUCTION OF 1,3-BUTADIENE IN THE PRESENCE OF A TANTALUM OXIDE DOPED BY AN ALDOLIZING ELEMENT

PRIOR ART

Butadiene is widely used in the chemical industry, in particular as a reagent for the production of polymers. Currently, butadiene is almost entirely produced from steam-cracking units, of which it constitutes an upgradeable by-product. The price fluctuation of petroleum and the ever-increasing demand for this chemical intermediate product made its price very volatile, which means that an effort should be made to diversify supply means. It is thus well known to one skilled in the art that 1,3-butadiene can be produced starting from ethanol. Two methods have been industrialized on a large scale: the "S. K. Process" and the "Carbide Process." In the "S. K. Process," 1,3-butadiene is produced from ethanol in one step, whereas in the "Carbide Process," 1,3-butadiene is produced in two steps: ethanol is first converted into acetaldehyde, and then an ethanol-acetaldehyde mixture is converted into 1,3-butadiene. The main distinction between the catalysts involved in these methods is that one (S. K. Process) is able to dehydrogenate ethanol into acetaldehyde while producing butadiene from the mixture that is thus formed whereas the other is not able to do so and therefore requires a first dehydrogenation step on a specific catalyst. The chemical elements that constitute the catalyst that are the most effective for this method for the production of butadiene are magnesium, tantalum, zirconium, hafnium, with butadiene selectivities between 50 and 69%, with niobium (or columbium) being considered as an element that is not very attractive with selectivities of less than 40% (B. B. Corson, H. E. Jones, C. E. Welling, J. A. Hinckley, E. E. Stahly *Ind. Eng. Chem.*, 1950, 42 (2), pp. 359-373).

Regardless of the method (one or two steps), the overall balance of the main reaction is written as follows:

$2CH_3CH_2OH \rightarrow CH_2CHCHCH_2+H_2+2H_2O$

Underlying this overall balance are numerous chemical reactions that comprise a dehydrogenation reaction that makes it possible to generate acetaldehyde (I), a reaction for aldolization/crotonization of acetaldehyde into crotonaldehyde (II), a Meerwein-Ponndorf-Verley (MPV) reaction between ethanol and crotonaldehyde (III), and finally a step for dehydration of crotylic alcohol into butadiene (IV).

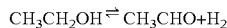
$CH_3CH_2OH \rightleftharpoons CH_3CHO+H_2$  I:

$2CH_3CHO \rightleftharpoons CH_3CHCH\text{—}CHO+H_2O$  II:

$CH_3CHCH\text{—}CHO+CH_3CH_2OH \rightleftharpoons CH_3CHCH\text{—}CH_2OH+CH_3CHO$  III:

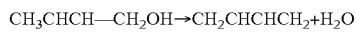
$CH_3CHCH\text{—}CH_2OH \rightarrow CH_2CHCHCH_2+H_2O$  IV:

This multiplicity of chemical reactions is at the origin of numerous by-products if the linking of steps is not done in the order specified above, with in particular the presence of secondary condensation and dehydration reactions. In addition, other reactions can take place (such as isomerization, cyclization, the Diels-Alder reaction, etc.), also increasing the number of by-products. In this stage, we note that, depending on the nature of the catalyst used for the transformation of ethanol (or of the ethanol-acetaldehyde mixture) into 1,3-butadiene, the distribution of said by-products can greatly vary. Thus, the addition of an acidic element will make the production of dehydration products (for example, ethylene or diethyl ether) increase, while the addition of a basic element will promote the formation of multiple condensation products (for example, hexenes or hexadienes).

Consequently, regardless of the method (one or two steps), the selectivity of the transformation of ethanol (or of the ethanol-acetaldehyde mixture) into 1,3-butadiene is moderate. However, because of the relatively high price of the raw material, the economic study of the method shows that the effectiveness of the transformation of the feedstock constitutes a significant lever for ensuring its viability. Numerous efforts have therefore been made to maximize this selectivity.

In particular, during the development of the method for the production of butadiene from an ethanol/acetaldehyde mixture (two-step method), the best catalyst found was a tantalum oxide deposited on an amorphous silica (Ind. Eng. Chem. 41 (1949), pages 1012-1017). The selectivity of butadiene was 69% for an initial conversion of the feedstock of 34%. It was also shown that the use of this same catalyst in a "Carbide" industrial unit led to the formation of the following majority impurities (by-products): diethyl ether (23% by weight of impurities), ethylene (11% by weight of impurities), hexenes, hexadienes (11% by weight of impurities), etc. (W. J. Toussaint, J. T. Dunn, D. R. Jackson, *Industrial and Engineering Chemistry* Vol. 39, No. 2, pp. 120-125, 1947). Despite the presence of by-products, their formation is limited by the relatively weak acido-basicity properties of the tantalum element. The latter also makes it possible to catalyze the reactions II, III and IV very effectively.

However, this property of the tantalum element is also one of the reasons that explains the difficulty encountered for maintaining the same selectivity throughout a catalytic cycle, with a catalytic cycle corresponding to the time taken under load between two regeneration phases of the catalyst. Actually, with the aging of the catalyst and its coking, the catalyst loses a portion of its active sites. The selectivity of the catalyst can be profoundly affected by it, especially since all of the active sites that are involved are not equivalent. In the case of this method where the selectivity is the primary factor impacting the performances, the duration of a catalytic cycle, i.e., the period when the method is selective enough to be economically profitable, can thus be greatly reduced.

Several solutions have been envisioned for limiting or circumventing this problem of deactivating the catalyst, such as, for example, the installation of continuous regenerative methods (fluidized beds, etc.) that make it possible to avoid these problems of controlling the deactivation. However, the installation of such a technology greatly increases the cost of the method. Another proposed solution was to add continuously an oxidizing element (such as oxidized water) that, in addition to modifying the balance of the various chemical reactions, is to act as a decoking element.

SUMMARY OF THE INVENTION

The invention relates to a catalyst that comprises—and preferably consists of—at least the tantalum element, at least an aldolizing element that is selected from the group that consists of magnesium, calcium, barium, cerium and tin and mixtures thereof, and at least one mesoporous oxide matrix that comprises at least one oxide of an element X that is selected from among silicon, titanium and mixtures thereof, with the mass of the tantalum element consisting of between 0.1 and 30% of the mesoporous oxide matrix mass, with the aldolizing element mass being between 0.02 and 4% of the mesoporous oxide matrix mass, and use thereof.

Advantage of the Invention

The advantage of the invention is to maintain the high selectivity of the tantalum element for the production of butadiene from a mixture that comprises at least ethanol via the addition of an inherently not very selective co-element for the production of butadiene. The applicant actually discovered that, surprisingly enough, a subtle combination of a preferably aldolizing element, selected from among the following non-exhaustive list: magnesium, calcium, barium, lanthanum, cerium and tin, with tantalum makes it possible to compensate for the loss of selectivity of the catalyst. This discovery thus makes it possible to improve the performances of the method, either by limiting the losses during a given service life (limited production of by-products over the same time period) or by increasing this service life (selectivity kept at an economically acceptable level over a longer time period).

Hereinafter, aldolizing element is defined as an element that is selected from the following non-exhaustive list: magnesium, calcium, barium, cerium and tin. In a preferred manner, the aldolizing element is selected from the group that consists of magnesium, calcium, barium, cerium and tin, and mixtures thereof.

DISCLOSURE OF THE INVENTION

This invention relates to the combination, in the same catalyst, of the tantalum element with a metal element called an aldolizing element, selected from the following non-exhaustive list: magnesium, calcium, barium, cerium and tin, in a method for the production of butadiene from a feedstock that comprises at least ethanol. This combination is manifested by an improvement in the performances of the catalyst according to the invention over a given duration, in comparison to the performances of an ordinary catalyst based on tantalum alone.

This invention therefore makes it possible to improve in a significant way the method for the production of butadiene, either by limiting the losses of raw materials in the form of undesirable by-products during a given work period, or by increasing potentially the service life of the catalyst with iso-selectivity.

The invention relates to a catalyst, used for the production of butadiene from a feedstock that comprises at least ethanol, comprising at least the tantalum element combined with at least one aldolizing element and at least one mesoporous oxide matrix, with said aldolizing element, also called co-element, being selected from the following non-exhaustive list: magnesium, calcium, barium, cerium and tin, preferably in the group that consists of magnesium, calcium, barium, cerium and tin and mixtures thereof, in a preferred manner in the group that consists of Mg, Ca, Ba, Ce and Sn and mixtures thereof. Preferably, said aldolizing element is selected from the group that consists of calcium and barium and mixtures thereof.

The catalyst according to the invention comprises a tantalum element mass of between 0.1 and 30%, preferably between 0.3 and 10%, in a preferred way between 0.5 and 5%, and in a very preferred manner between 0.5 and 2% of the mesoporous oxide matrix mass.

The catalyst according to the invention comprises a co-element mass of between 0.02 and 4%, preferably between 0.02 and 2%, in a preferred way between 0.05 and 1%, and in a very preferred manner between 0.05 and 0.5% of the mesoporous oxide matrix mass.

Catalyst comprising an element A, with the mass of the element A being—or representing—between x and y % of the mesoporous oxide matrix mass, is defined as said catalyst comprising between x and y parts by weight of said element A per 100 parts by weight of said mesoporous oxide matrix.

The catalyst according to the invention also advantageously comprises at least one element that is selected from the group that consists of the elements of groups 1, 4, 5 of the periodic table and mixtures thereof, in a preferred way of at least one element that is selected from the group that consists of the element Cs and the element Nb and mixtures thereof, and in a very preferred manner the element Nb, with the mass of said element representing between 0.01 and 5%, preferably between 0.01 and 1%, in a preferred way between 0.05 and 0.5% of the mesoporous oxide matrix mass. In a very preferred manner, said catalyst according to the invention does not comprise Nb.

In a particular arrangement, the catalyst according to the invention advantageously also comprises at least one element that is selected from the group that consists of the elements of groups 11 and 12 of the periodic table and mixtures thereof, i.e., the periodic table of elements, in a more preferred way at least one element that is selected from group 12 of the periodic table and in an even more preferred way the Zn element, with the mass of said element representing between 0.5 and 10%—and preferably between 1 and 5%—of the mass of said silica-based mesoporous oxide matrix. This arrangement is particularly advantageous in the case where the catalyst according to the invention is used in a one-step method, i.e., in a method that processes a feedstock that comprises primarily ethanol. Primarily ethanol is defined as the ratio by mass of ethanol to acetaldehyde in said feedstock, when said feedstock comprises acetaldehyde, being at least greater than 1, preferably at least greater than 5, with said feedstock also able to not comprise acetaldehyde.

The matrix of the catalyst according to the invention is mesoporous and comprises at least one oxide of an element X that is selected from among silicon, titanium and mixtures thereof. Preferably, the element X is silicon. Said oxide matrix is mesoporous, i.e., it is characterized by the presence of pores whose size varies between 2 and 50 nm according to the IUPAC classification (K. S. W. Sing; D. H. Everett; R. A. W. Haul; L. Moscou; J. Pierotti; J. Rouquerol; T. Siemieniewska, *Pure Appl. Chem.*, 57, 603, 1985). In addition to being mesoporous, said matrix can be mesostructured (i.e., can have mesopores of uniform size and distributed in a periodic way in said matrix) or else have hierarchized porosity (presence of micropores and/or macropores in addition to mesopores). In a very preferred way, the mesoporous oxide matrix that constitutes the catalyst according to the invention is a mesoporous amorphous silica with a non-organized porosity without micropores.

More particularly, the matrix of the catalyst according to the invention comprises a silicon oxide (silica) that has a specific surface area of 100 to 1,200 m$^2$/g, and preferably at least 400 m$^2$/g, a mesopore volume of between 0.2 and 1.8 ml/g, and preferably at least 0.6 ml/g, and a mesopore diameter of between 4 and 50 nm, and preferably at least 6 nm. It is possible to use, for example, a Davisil Grade 636 commercial silica (SBET≈500 m$^2$/g, Vp≈0.9 ml/g and φ≈7 nm). In an advantageous manner, said matrix of the catalyst according to the invention does not undergo acidic washing.

More particularly, the silicon oxides, also called silicas, which contain contents of alkaline metals that are expressed in terms of % by weight of metal in relation to the mass of the mesoporous matrix and that are less than 1% by weight, preferably less than 0.5% by weight, and in a very preferred way less than 0.1% by weight, are used.

The catalyst according to the invention can be prepared according to the methods that are known to one skilled in the art. The tantalum element, the aldolizing element, just like the optional additional element, constituting the catalyst according to the invention, can therefore be introduced by any method that is known to one skilled in the art and at any step of the preparation of the catalyst according to the invention.

Thus, the tantalum element, the aldolizing element, just like the optional additional element of the catalyst according to the invention, can be introduced by depositing combined precursors on the surface of a preformed mesoporous oxide matrix. The latter can be commercial or else custom-synthesized according to the methods that are known to one skilled in the art, in particular by using so-called "sol-gel" synthesis methods (see the definition below). For example, and in a non-exhaustive way, the methods called dry impregnation, excess impregnation, CVD (Chemical Vapor Deposition or chemical deposition in the vapor phase), and CLD (Chemical Liquid Deposition or chemical deposition in the liquid phase), etc., can be employed.

Another option consists in using as a method for preparation of the catalyst according to the invention any of the synthesis methods that are known to one skilled in the art, making it possible to introduce the precursors that are combined with the tantalum element, the aldolizing element, just like those combined with the optional additional element, directly during the synthesis of the selected mesoporous oxide matrix. For example and in a non-exhaustive way, the synthesis methodologies that are employed can be inorganic "traditional" synthesis methods (precipitation/gelling from salts under mild temperature and pressure conditions) or metallo-organic "modern" methods (precipitation/gelling from alkoxides under mild temperature and pressure conditions), with the latter able to be referred to in a simplified way as "sol-gel" methods. It is also possible to use "sol-gel" methods that are combined with the use of specific synthesis methods such as spray-drying (also called atomization), dip-coating, etc.

A third option consists in introducing the tantalum element directly during the synthesis of the selected mesoporous oxide matrix and the aldolizing co-element by deposition of at least one precursor that is attached to the surface of the mesoporous oxide matrix that contains tantalum and vice versa. The optional additional element is itself introduced interchangeably with the tantalum element or with the aldolizing co-element.

According to a preferred embodiment of this invention, the methods that make it possible to ensure the best dispersion of the tantalum element, the aldolizing co-element, just like the optional additional element, are selected so as to maximize the productivity and the selectivity of the catalyst according to the invention.

For a deposition of the precursors of these elements on the surface of the preformed mesoporous oxide matrix, the so-called dry impregnation method is preferred. No particular limitation exists relative to the number of times that said dry impregnation step is repeated. The various steps can be carried out using one or more solvents or mixture of solvents in which the precursors of the tantalum element, the aldolizing co-element, just like the optional additional element, are soluble. These solvents can be polar/protic such as water, methanol or ethanol, polar/aprotic such as toluene or xylene, or apolar/aprotic such as hexane. The acidity of the solutions can also be adapted (addition of acid) to improve the solubility of the radicals. Likewise, each of the elements from among the tantalum element, the aldolizing co-element, and the optional additional element can be impregnated by itself or else co-impregnated with at least one of the other elements, with the sole limitation being the joint presence of the tantalum element and the aldolizing co-element at the end of the method for preparation of the catalyst according to the invention. A preferred mode consists in carrying out a first dry impregnation of the aldolizing co-element and then, consecutively, a second dry impregnation of the tantalum element. A dry-impregnation-type step comprises, for example, the following operations:

(a) Dissolution of at least one precursor of the tantalum element, at least one precursor of the aldolizing co-element, and optionally at least one precursor of the additional element in a solution volume that corresponds to the pore volume of the preformed mesoporous oxide matrix that is selected, (b) Impregnation of the solution that is obtained during the operation (a) on the surface of the preformed mesoporous oxide matrix that is selected, (c) Optional curing of the solid that is thus obtained in an atmosphere and at a temperature that are controlled in such a way as to promote the dispersion of at least said precursors that are used according to the invention over the entire surface of the preformed mesoporous oxide matrix that is selected, (d) Optional (hydro)thermal post-treatment(s) of the solid that is obtained during the operation (c) (drying and/or calcination, and/or steaming, etc.) in such a way as to obtain an intermediate solid or, ultimately, the catalyst according to the invention.

For an introduction of precursors combined with the tantalum element and an aldolizing co-element, just like those combined with the optional additional element, directly during the synthesis of the mesoporous oxide matrix, the methods for "sol-gel" synthesis by precipitation and atomization are preferred. In an even more preferred way, the method for "sol-gel" synthesis by precipitation is favored.

In the particular case of a sol-gel synthesis by precipitation leading to obtaining a catalyst that is characterized by a matrix based on mesoporous oxide with a non-organized porosity, the method for preparation of said catalyst according to the invention comprises, for example, the following operations:

a) Dissolution of at least one precursor of at least the element X that constitutes the mesoporous oxide matrix that is selected in aqueous, organic or aquo-organic medium, optionally in the presence of an acid or a base, in such a way as to form an optionally colloidal solution, b) Addition to the solution that is obtained during the operation (a) of at least one precursor of the tantalum element, at least one precursor of the aldolizing co-element, and optionally at least one precursor of the additional element, in the pure state or dissolved in a suitable medium that is compatible with said solution that is obtained from operation (a). Operation (b) can be repeated as many times as necessary, in particular during the addition, which occurs at different times, of the various tantalum elements, aldolizing co-element and the optional additional element, c) Precipitation of the mesoporous oxide matrix that is selected and that contains the tantalum element, the aldolizing co-element, and the optional additional element by the addition of an acid, a base, or by application of a specific reaction temperature, d) Filtration followed by optional washing cycles or evaporation of the suspension that is obtained during the operation (c), e) (Hydro)thermal post-treatment(s) of the solid that is obtained in step (d) (drying and calcination, or steaming, etc.) in such a way as to obtain the catalyst that is used according to the invention.

The precursor(s) of at least said element X that is selected from among silicon, titanium and their mixtures of the mesoporous oxide matrix, used during the operation (a), can be any compound that comprises the element X and that can release this element in solution in reactive form. Thus, the precursor(s) of at least said element X is (are) advantageously an inorganic salt of said element X of formula $XZ_n$, (n=3 or 4), with Z being a halogen, the group $NO_3$, or a perchlorate. The precursor(s) of at least said element X that is/are being considered can also be (an) alkoxide precursor(s) of formula $X(OR)_n$, where R=ethyl, isopropyl, n-butyl, s-butyl, t-butyl, etc., or a chelated precursor such as $X(C_5H_8O_2)_n$, with n=3 or 4. The precursor(s) of at least said element X that is/are being considered can also be (an) oxide(s) or (a) hydroxide(s) of said element X. In the preferred case where X is silicon, the silicic precursor is obtained from any silica source and advantageously from a sodium silicate precursor of formula $Na_2SiO_3$, a chlorinated precursor of formula $SiCl_4$, an alkoxide precursor of formula $Si(OR)_4$ where R=H, methyl, ethyl or a chloroalkoxide precursor of formula $Si(OR)_{4-a}Cl_a$ where R=H, methyl, ethyl, with a being between 0 and 4. The silicic precursor can also advantageously be an alkoxide precursor of formula $Si(OR)_{4-a}R'_a$, where R=H, methyl, ethyl and R' is an alkyl chain or an alkyl chain that is functionalized, for example, by a thiol, amino, β diketone, or sulfonic acid group, with a being between 0 and 4. A preferred silicic precursor is tetraethyl orthosilicate (TEOS).

Regardless of the method for incorporating the tantalum element, the aldolizing co-element and the optional additional element, the precursors of the latter are any compound that comprises at least the tantalum element, the co-element or the optional additional element and that can release this element in solution in reactive form. Thus, the precursors of at least the tantalum element, the aldolizing co-element or the optional additional element are advantageously inorganic salts and alkoxide precursors. The inorganic salts are selected from the group that consists of the halides, the nitrates, the sulfates, the phosphates, the hydroxides, the carbonates, the carboxylates, the alcoholates, and combinations of two or more of the former, more preferably selected from the group that consists of the chlorides, the nitrates, the carboxylates, the alcoholates, and combinations of two or more of the former. The alkoxide precursors have for a formula, for example, $M(OR)_n$, where M=Nb, Ta, etc., and R=ethyl, isopropyl, n-butyl, s-butyl, t-butyl, etc., or a chelated precursor such as $X(C_5H_8O_2)_n$, with n=3 or 4. For example, the preferred precursors of tantalum are tantalum pentachloride and tantalum pentaethanoate, which can be used with most organic solvents.

The catalyst according to the invention can be shaped in the form of balls, pellets, granules, or extrudates (cylinders that may or may not be hollow, multilobed cylinders with 2, 3, 4 or 5 lobes for example, twisted cylinders), or rings, etc., with these shaping operations being carried out by the conventional techniques that are known by one skilled in the art. Preferably, said catalyst that is used according to the invention is obtained in the form of extrudates of a size of between 1 and 10 mm. However, it is not impossible that said materials that are obtained will then be, for example, introduced into a piece of equipment that makes it possible to round their surfaces, such as a bezel or any other piece of equipment that makes it possible to make them spherical in shape.

During the shaping operation, the catalyst according to the invention can optionally be mixed with at least one porous oxide material that has the role of binder so as to generate the physical properties of the catalysts that are suited to the method (mechanical strength, resistance to attrition, etc.).

Said porous oxide material is preferably a porous oxide material that is selected from the group that is formed by silica, magnesia, clays, titanium oxide, lanthanum oxide, cerium oxide, boron phosphates, and a mixture of at least two of the oxides cited above. It is also possible to use titanates, for example the titanates of zinc, nickel, cobalt. It is also possible to use simple, synthetic or natural clays of the 2:1 dioctahedral phyllosilicate type or the 3:1 trioctahedral phyllosilicate type such as kaolinite, antigorite, chrysotile, montmorillonnite, beidellite, vermiculite, talc, hectorite, saponite, laponite. These clays can optionally be delaminated. The various mixtures that use at least two of the compounds cited above are also suitable for ensuring the binder role.

In a very preferred way, the binder that is used has a silicic nature. For example and in a non-exhaustive way, said silicic binder can be in the form of colloidal solutions or powders.

Preferably, said catalyst comprises 5 to 60% by weight, and in a preferred manner between 10 and 30% by weight, of silicic binder, with the percentages by weight being expressed in relation to the total mass of said catalyst.

Optionally, at least one organic adjuvant is also mixed during said shaping step. The presence of said organic adjuvant facilitates the shaping by extrusion. Said organic adjuvant can advantageously be selected from among methyl cellulose, hydroxypropyl methylcellulose, hydroxyethyl cellulose, carboxymethylcellulose, and polyvinyl alcohol. The proportion of said organic adjuvant is advantageously between 0 and 20% by weight, preferably between 0 and 10% by weight, and in a preferred manner between 0 and 7% by weight, in relation to the total mass of said shaped material.

Based on the method for preparation of the catalyst that is selected, it is also possible to carry out said shaping step directly on the mesoporous oxide matrix of the catalyst according to the invention. In this case, the introduction of the tantalum element, the aldolizing co-element, and the optional additional element is carried out as described above via a deposition of precursors of these elements on the surface of the preformed and shaped mesoporous oxide matrix.

Regardless of the method for incorporating tantalum elements, the aldolizing co-element and the optional additional element in the catalyst according to the invention, and regardless of the shaping steps that are selected, a (hydro) thermal post-treatment step (drying and/or calcination, and/ or steaming, etc.) is applied in such a way as to obtain the catalyst according to the invention. Preferably, the applied post-treatment is a calcination in air in an oven in a temperature range of 300 to 800° C., in a preferred way from T=450° C. to T=700° C. and in an even more preferred way from T=540° C. to T=700° C., for a period of less than 24 hours and preferably less than 12 hours.

The nitrogen volumetric analysis corresponding to the physical adsorption of nitrogen molecules in the porosity of the catalyst according to the invention via a gradual increase in pressure at constant temperature provides information on the particular textural characteristics (pore diameter, pore volume, specific surface area) of the material that is used according to the invention. In particular, it makes it possible to access the specific surface area and the mesopore distribution of the catalyst. Specific surface area is defined as the BET specific surface area (SBET in $m^2/g$) that is determined by nitrogen adsorption in accordance with the ASTM D 3663-78 standard established from the BRUNAUER-EMMETT-TELLER method described in the periodical "The Journal of American Society," 1938, 60, 309. The pore distribution that is representative of a mesopore population centered in a range of from 2 to 50 nm (IUPAC classification) is determined by the Barrett-Joyner-Halenda (BJH) model. The nitrogen adsorption-desorption isotherm according to the BJH model that is thus obtained is described in the periodical "The Journal of American Society," 1951, 73, 373, written by E. P. Barrett, L. G. Joyner and P. P. Halenda. In the following disclosure of the invention, nitrogen adsorption volume is defined as the volume that is measured for P/P0=0.99, pressure for which it is assumed that nitrogen has filled all of the pores. In the following disclosure, the diameter of mesopores f of the oxide-based matrix corresponds to the value of the maximum diameter that is read on the pore size distribution curve obtained from the adsorption branch of the nitrogen isotherm. In addition, the form of the nitrogen adsorption isotherm and the hysteresis loop can provide information on the nature of the mesoporosity and the presence of the possible microporosity of the catalyst according to the invention. The quantitative analysis of the microporosity of the inorganic material that is obtained according to the invention is carried out from methods "t" (Lippens-De Boer method, 1965) or "$\alpha_s$" (method proposed by Sing) that correspond to transforms of the initial adsorption isotherm as described in the work "Adsorption by Powders and Porous Solids. Principles, Methodology and Applications" written by F. Rouquerol, J. Rouquerol and K. Sing, Academic Press, 1999. These methods make it possible to access in particular the value of the characteristic micropore volume of the microporosity of the catalyst according to the invention.

In the following disclosure of the invention, the pore distribution that is measured by mercury porosimetry is determined by mercury porosimeter intrusion according to the ASTM D4284-83 standard at a maximum pressure of 4,000 bar (400 MPa), using a surface tension of 484 dyne/cm and a contact angle of 140°. The wetting angle was assumed to be equal to 140° by following the recommendations of the work "Techniques de l'ingénieur, traité analyse et caractérisation [Engineering Techniques, Analytical Treatise and Characterization], pp. 1050-5, written by Jean Charpin and Bernard Rasneur."

The value beyond which the mercury fills all of the intergranular gaps is set at 0.2 MPa, and it is considered that beyond this, the mercury penetrates into the pores of the alumina.

So as to obtain a better precision, the value of the total pore volume corresponds to the value of the total pore volume that is measured by mercury porosimeter intrusion that is measured on the sample minus the value of the total pore volume that is measured by mercury porosimeter intrusion that is measured on the same sample for a pressure that corresponds to 30 psi (approximately 0.2 MPa).

The macropore volume of the catalyst is defined as being the cumulative volume of mercury that is introduced at a pressure of between 0.2 MPa and 30 MPa, corresponding to the volume that is contained in the pores with an apparent diameter of greater than 50 nm.

The mesopore volume of the catalyst is defined as being the cumulative volume of mercury that is introduced at a pressure of between 30 MPa and 400 MPa, corresponding to the volume that is contained in the pores with an apparent diameter of between 2 and 50 nm.

Another object of the invention is the use of a catalyst that comprises at least the tantalum element, the aldolizing co-element, and at least one mesoporous oxide matrix for the conversion of a feedstock that comprises at least ethanol into butadiene, manifested by significant performance advantages in terms of productivity and selectivity. The representative conditions for this reaction (conditions for which a better productivity and a better selectivity are observed) are a temperature of between 300 and 400° C., preferably between 320° C. and 380° C., a pressure of between 0.15 and 0.5 MPa, preferably between 0.15 and 0.3 MPa, a volumetric flow rate of between 0.5 and 5 $h^{-1}$, preferably between 1 and 4 $h^{-1}$, and, in the case of the "two-step" method where the feedstock comprises ethanol and acetaldehyde, a ratio by mass of ethanol/acetaldehyde of between 1 and 30, in a preferred manner between 2 and 10. The volumetric flow rate is defined as the ratio between the mass flow rate of the feedstock and the catalyst mass.

The invention is illustrated by means of the following examples.

EXAMPLES

Description of the Dry Impregnation Method for the Deposition of Tantalum

The basic silicic substrate before the impregnation steps is the Davisil grade 636 silica that is produced (SBET≈500 $m^2/g$, Vp≈0.9 ml/g and φ≈7 nm, grain size: 200-500 microns).

The tantalum pentaethoxide ($Ta(OCH_2CH_3)_5$) (whose quantity is calculated from the Ta content to be deposited on the substrate) is diluted in an ethanol solution (whose quantity is proportional to the pore volume of the silicic substrate). This solution is quickly added drop by drop and mixed with the silicic substrate until wettability of the surface of the latter (dry impregnation) is observed. The solid is then placed in an ethanol-saturated atmosphere for 3 hours, dried at 100° C. for 24 hours. The catalyst is obtained by calcination of the solid that is dried in air at 550° C. for 4 hours.

Description of the Dry Impregnation Method for the Deposition of Other Elements

The precursor of the element that is to be deposited whose quantity is calculated from the content of the element that is to be deposited on the substrate is diluted in an aqueous solution whose quantity is proportional to the pore volume of the silicic substrate. This solution is quickly added drop by drop to the silicic substrate until wettability of the surface of the latter (dry impregnation) is observed. The solid is then placed in a water-saturated atmosphere for 3 hours, dried at 100° C. for 24 hours. The catalyst is obtained by calcination of the solid that is dried in air at 550° C. for 4 hours.

| Element to be Deposited | Precursor that is Used |
| --- | --- |
| Nb | $C_4H_4NNbO_9 \cdot 5H_2O$ |
| Zr | $ZrOCl_2 \cdot 8H_2O$ |
| Zn | $Zn(NO_3)_2 \cdot 6H_2O$ |
| Ag | $AgNO_3$ |
| Ca | $Ca(NO_3)_2 \cdot 4H_2O$ |
| Ba | $Ba(NO_3)_2$ |
| Mg | $Mg(NO_3)_2 \cdot 6H_2O$ |
| Ce | $Ce(NO_3)_3 \cdot 6H_2O$ |
| La | $La(NO_3)_3 \cdot 6H_2O$ |
| Sn | $SnCl_3$ |
| Cs | $CsNO_3$ |
| In | $In(NO_3)_3$ |
| Mo | $(NH_4)_6Mo_7O_{24} \cdot 4H_2O$ |

Description of the Catalytic Test Unit

The reactor that is used in the following examples consists of a stainless steel tube that is 20 cm long and 10 mm in diameter. The reactor is first loaded with carborundum and then with the catalyst that is diluted in carborundum and finally with carborundum. The carborundum is inert relative to the feedstock and does not influence the catalytic results; it makes it possible to position the catalyst in the isothermal zone of the reactor and to limit the risks of material and heat transfer problems. The temperature of the reactor is controlled with a tubular furnace with three heating zones. The liquid feedstock (mixture of ethanol and acetaldehyde in a ratio R) is injected via a double-piston HPLC pump. The liquid stream is evaporated in the lines that are heated by a tracer before entering into the reactor and is homogenized by passing into a static mixer. The products that are formed during the reaction are kept in the vapor phase so that they can be analyzed on-line by gas chromatography (PONA and Carboxen 1010 capillary columns) to make possible the most precise identification of the hundreds of products formed. The catalyst is activated in situ under nitrogen at the test temperature. The specific operating conditions are described in the following examples.

Definition of the Terms

Conversion (% by weight):

$$\text{conversion} = 100 * \left(1 - \frac{\text{mass flow rate of exiting ethanol} + \text{mass flow rate of exiting acetaldehyde}}{\text{mass flow rate of entering ethanol} + \text{mass flow rate of entering acetaldehyde}}\right)$$

Selectivity (% C):

$$\text{selectivity} = \frac{\text{mass flow rate of carbon belonging to butadiene } (gc/h)}{\text{mass flow rate of carbon belonging to the converted feedstock}}$$

Example 1: Comparison in the Absence of Tantalum of the Behavior of the Aldolizing Co-Elements in Contact with a Low-Acetaldehyde Feedstock In this test example, the ethanol/acetaldehyde ratio of the feedstock is set at 24 mol/mol, the temperature at 350° C., and the pressure at 1.5 bar. For each catalyst, the feedstock flow rate is adjusted to obtain a stable conversion of 45%. The carbon selectivity values are measured at this operating point after a time under load of 2 hours.

| According to the Invention | Catalyst | Main Element for the Production of Butadiene (% by Weight) | Co-Element (% by Weight) | Additional Element (% by Weight) | Butadiene Selectivity | Selectivity of Aldolization Products (Crotonaldehyde, Hexadienals) |
|---|---|---|---|---|---|---|
| For Comparison Purposes | A | Ta (2%) | — | Zn (1%) | 68% | 1% |
| For Comparison Purposes | A' | — | | Zn (1%) | 31% | 17% |
| No | B1 | — | Ca (1.5%) | Zn (1%) | 25% | 26% |
| No | B2 | — | Ba (1.5%) | Zn (1%) | 24% | 35% |
| No | B3 | — | Ce (0.75%) | Zn (1%) | 20% | 28% |
| No | B4 | — | Mg (2%) | Zn (1%) | 29% | 25% |
| No | B5 | — | Sn (0.75%) | Zn (1%) | 22% | 26% |

If the co-element (Ca, Ba, Ce, Mg, Sn) is not combined with tantalum, it is not capable, under the test conditions, to produce the butadiene selectively in comparison to the tantalum-based catalyst, but acts primarily as an aldolization catalyst.

Example 2: Comparison in the Presence of Tantalum of the Impact of Co-Elements in Contact with a Low-Acetaldehyde Feedstock with Feedstock Flow Rate Variation In this example, the ethanol/acetaldehyde ratio of the feedstock is set at 24 mol/mol, the temperature at 350° C., and the pressure at 1.5 bar. For each catalyst, the feedstock flow rate is adjusted to obtain a stable conversion of 45%. The selectivity values are measured at this operating point after 2 and 48 hours of testing.

| According to the Invention | Catalyst | Main Element for the Production of Butadiene (% by Weight) | Aldolizing Co-Element (% by Weight) | Additional Element 1 (% by Weight) | Additional Element 2 (% by Weight) | Initial Butadiene Selectivity after 2 Hours | Loss of Butadiene Selectivity after 48 Hours |
|---|---|---|---|---|---|---|---|
| For Comparison Purposes | A | Ta (2%) | — | Zn (1%) | — | 68% | 1 |
| Yes | F | Ta (2%) | Ca (0.5%) | Zn (1%) | — | 68% | 0.3 |
| Yes | G | Ta (2%) | Ca (1.5%) | Zn (1%) | — | 66% | 0.1 |
| Yes | H | Ta (2%) | Sn (0.25%) | Zn (1%) | — | 66% | 0.7 |
| Yes | I | Ta (2%) | Sn (0.75%) | Zn (1%) | — | 66% | 0.4 |
| Yes | J | Ta (2%) | Ce (0.25%) | Zn (1%) | — | 65% | 0.5 |
| Yes | K | Ta (2%) | Ce (0.75%) | Zn (1%) | — | 66% | 0.8 |
| Yes | L | Ta (2%) | Mg (0.5%) | Zn (1%) | — | 67% | 0.2 |
| No | M | Ta (2%) | La (0.75%) | Zn (1%) | — | 66% | 1.1 |
| No | N | Ta (2%) | In (0.75%) | Zn (1%) | — | 59% | 1.5 |
| No | O | Ta (2%) | Mo (0.75%) | Zn (1%) | — | 60% | 1.4 |
| For Comparison Purposes | A | Ta (2%) | — | Zn (2%) | — | 67% | 2.9 |
| Yes | P | Ta (2%) | Sn (0.25%) | Zn (2%) | — | 67% | 2.2 |
| Yes | Q | Ta (2%) | Ce (0.25%) | Zn (2%) | — | 66% | 2.3 |
| No | R | Ta (2%) | La (0.25%) | Zn (2%) | — | 66% | 3.1 |
| No | S | Ta (2%) | La (0.75%) | Zn (2%) | — | 65% | 3.9 |
| For Comparison Purposes | T | Ta (2%) | — | Zn (1%) | Cs (0.2%) | 69% | 1.3 |
| Yes | U | Ta (2%) | Ca (0.25%) | Zn (1%) | Cs (0.2%) | 69% | 0.6 |

-continued

| According to the Invention | Catalyst | Main Element for the Production of Butadiene (% by Weight) | Aldolizing Co-Element (% by Weight) | Additional Element 1 (% by Weight)) | Additional Element 2 (% by Weight) | Initial Butadiene Selectivity after 2 Hours | Loss of Butadiene Selectivity after 48 Hours |
|---|---|---|---|---|---|---|---|
| For Comparison Purposes | V | Ta (2%) | — | | Ag (2.5%) | 67% | 6.8 |
| Yes | W | Ta (2%) | Ce (0.25%) | | Ag (2.5%) | 66% | 3.1 |
| Yes | X | Ta (2%) | Mg (0.75%) | | Ag (2.5%) | 67% | 2.8 |

This example demonstrates that the presence of suitable co-elements (Ca, Ba, Ce, Mg, Sn), when they are combined with tantalum, makes it possible to keep the butadiene selectivity level at a high and stable value over a longer period of time.

Example 3: Comparison with a Low-Acetaldehyde Feedstock of the Impact of Aldolizing Co-Elements in the Presence of an Element for the Production of Butadiene Other than Tantalum In this example, the ethanol/acetaldehyde ratio of the feedstock is set at 24 mol/mol, the temperature at 350° C., and the pressure at 1.5 bar. For each catalyst, the feedstock flow rate is adjusted to obtain a stable conversion of 45%. The selectivity values are measured at this operating point after 2 and 48 hours of testing.

| According to the Invention | Catalyst | Main Element for the Production of Butadiene (% by Weight) | Aldolizing Co-Element (% by Weight) | Additional Element (% by Weight) | Initial Selectivity | Loss of Selectivity in 48 Hours |
|---|---|---|---|---|---|---|
| For Comparison Purposes | Y | Zr (0.5%) | — | Zn (1%) | 63% | 1.5 |
| No | Z | Zr (0.5%) | La (0.25%) | Zn (1%) | 62% | 1.6 |
| No | AA | Zr (0.5%) | Ce (0.25%) | Zn (1%) | 61% | 1.9 |
| No | AB | Zr (0.5%) | Ce (0.75%) | Zn (1%) | 62% | 1.5 |
| For Comparison Purposes | AC | Zr (0.5%) | — | Zn (2%) | 63% | 1.8 |
| No | AD | Zr (0.5%) | Mg (0.25%) | Zn (2%) | 61% | 2.1 |
| For Comparison Purposes | AE | Zr (0.5%) | — | Ag (1%) | 63% | 1.6 |
| No | AF | Zr (0.5%) | Sn (0.25%) | Ag (1%) | 63% | 2.2 |

Only the tantalum element appeared to benefit from the provision of the aldolizing co-element. When the catalyst contains only one other element for the production of butadiene such as zirconium, the impact of the co-element is zero or negative.

Example 4: Comparison in the Presence of Tantalum of the Impact of Co-Elements in Contact with a Low-Acetaldehyde Feedstock with Temperature Variation In this example, the ethanol/acetaldehyde ratio of the feedstock is set at 24 (mol/mol), the beginning test temperature at 350° C., and the pressure at 1.5 bar. For each catalyst, the feedstock flow rate is set to obtain a 45% conversion. Maintaining the conversion is ensured this time by a uniform increase in the temperature of the reactor. The selectivity values are measured after 5 and 72 hours of testing.

| According to the Invention | Catalyst | Main Element for the Production of Butadiene (% by Weight) | Aldolizing Co-Element (% by Weight) | Additional Element (% by Weight) | Selectivity of the Catalyst After 5 Hours | Loss of Selectivity After 72 Hours |
|---|---|---|---|---|---|---|
| For Comparison Purposes | A | Ta (2%) | — | Zn (1%) | 69.3 | 2.2 |
| Yes | F | Ta (2%) | Ca (0.5%) | Zn (1%) | 66.4 | 0.2 |
| Yes | AG | Ta (2%) | Sn (2%) | Zn (1%) | 69.5 | 1.6 |
| Yes | AH | Ta (2%) | Mg (1.5%) | Zn (1%) | 67.5 | 1.4 |

This example demonstrates that the presence of suitable co-elements, when they are combined with tantalum, makes it possible to keep the selectivity level at a high and stable value over a longer period of time and temperature.

Example 5: Comparison in the Absence of Tantalum of the Behavior of Aldolizing Co-Elements in Contact with an Acetaldehyde-Rich Feedstock In this example, the ethanol/acetaldehyde ratio of the feedstock is set at 2.5 (mol/mol), the temperature at 350° C., and the pressure at 1.5 bar. For each catalyst, the feedstock flow rate is adjusted to obtain a stable conversion of 25%. The carbon selectivity values are measured at this operating point after a time under load of 2 hours.

| According to the Invention | Catalyst | Main Element for the Production of Butadiene (% by Weight) | Aldolizing Co-Element (% by Weight) | Butadiene Selectivity | Selectivity of Aldolization Products |
|---|---|---|---|---|---|
| For Comparison Purposes | AI | Ta (2%) | — | 65% | 4% |
| No | AJ | — | Sn (1.5%) | 25% | 31% |
| No | AK | — | Ce (0.75%) | 18% | 36% |
| No | AL | — | Mg (1.5%) | 24% | 40% |
| No | AM | — | Ba (0.5%) | 10% | 60% |

The co-element, if it is not combined with tantalum, is not capable—under the test conditions—of producing butadiene selectively in comparison to the tantalum-based catalyst, but acts primarily as an aldolization catalyst.

Example 6: Comparison in the Presence of Tantalum of the Impact of Co-Elements in Contact with an Acetaldehyde-Rich Feedstock with a Feedstock Flow Rate Variation In this example, the ethanol/acetaldehyde ratio of the feedstock is set at 2.5 (mol/mol), the temperature at 350° C., and the pressure at 1.5 bar. For each catalyst, the feedstock flow rate is adjusted to obtain a stable conversion of 44%. The carbon selectivity values are measured at this operating point after a time under load of 2 and 48 hours.

| According to the Invention | Catalyst | Main Element for the Production of Butadiene (% by Weight) | Aldolizing Co-Element (% by Weight) | Additional Element (% by Weight) | Performances of the Catalyst After 2 Hours | Loss in Selectivity After 48 Hours |
|---|---|---|---|---|---|---|
| For Comparison Purposes | AN | Ta (5%) | — | — | 71% | 0.8 |
| Yes | AO | Ta (5%) | Ca (0.1%) | — | 71% | 0.2 |

-continued

| According to the Invention | Catalyst | Main Element for the Production of Butadiene (% by Weight) | Aldolizing Co-Element (% by Weight) | Additional Element (% by Weight) | Performances of the Catalyst After 2 Hours | Loss in Selectivity After 48 Hours |
|---|---|---|---|---|---|---|
| For Comparison Purposes | AP | Ta (0.5%) | — | Nb (0.25%) | 74% | 0.7 |
| Yes | AQ | Ta (0.5%) | Ca (0.1%) | Nb (0.25%) | 73% | 0.2 |

This example demonstrates that the presence of suitable co-elements, when they are combined with tantalum, makes it possible to keep the selectivity level at a high and stable value over a longer period of time.

Example 7: Comparison in the Presence of Tantalum of the Impact of Co-Elements in Contact with an Acetaldehyde-Rich Feedstock with Temperature Variation In this example, the ethanol/acetaldehyde ratio of the feedstock is set at 2.5 (mol/mol), the temperature at 350° C., and the pressure at 1.5 bar. For each catalyst, the feedstock flow rate is adjusted to obtain a stable conversion of 35%. The selectivity values are measured at this operating point after a time under load of 5 and 72 hours.

| According to the Invention | Catalyst | Main Element for the Production of Butadiene (% by Weight) | Aldolizing Co-Element (% by Weight) | Performances of the Catalyst After 5 Hours | Loss in Selectivity After 72 Hours |
|---|---|---|---|---|---|
| For Comparison Purposes | AN | Ta (5%) | — | 69% | 8.5 |
| Yes | AO | Ta (5%) | Ca (0.1%) | 70% | 4.9 |

This example demonstrates that the presence of suitable co-elements, when they are combined with tantalum, makes it possible to keep the selectivity level at a high and stable value over a longer period of time and temperature.

The invention claimed is:

1. A catalyst that comprises tantalum element an aldolizing element that is calcium, barium, or mixtures thereof, and at least one mesoporous oxide matrix that comprises at least one oxide of an element X that is silicon, titanium or mixtures thereof, with the mass of the tantalum element being between 0.1 and 30% of at least one mesoporous oxide matrix mass and the mass of the aldolizing element being between 0.02 and 4% of at least one the mass of the at least one mesoporous oxide matrix.

2. The catalyst according to claim 1, in which said aldolizing element is barium.

3. The catalyst according to claim 1, further comprising at least one element of Group 1, 4 or 5 of the periodic table, with element mass being between 0.01 and 5% of at least one mesoporous oxide matrix.

4. The catalyst according to claim 3, wherein the at least one element is Cs.

5. The catalyst according to claim 1, in which said at least one mesoporous oxide matrix is mesostructured.

6. The catalyst according to claim 1, in which said at least one mesoporous oxide matrix comprises a silicon oxide that has a specific surface area of 100 to 1,200 $m^2/g$, a mesopore volume of between 0.2 and 1.8 ml/g, and a mesopore diameter of between 4 and 50 nm.

7. The catalyst according to claim 1, further comprising at least one element of Group 11 or 12 of the periodic table or mixtures thereof, with at least element mass being between 0.5 and 10% of at least one mesoporous oxide matrix mass.

8. The catalyst according to claim 7, wherein the at least one element is Zn.

9. A process for a conversion of a feedstock that comprises at least ethanol into butadiene, comprising contacting said feedstock with the catalyst according to claim 1 at a temperature of between 300 and 400° C., a pressure of between 0.15 and 0.5 MPa, and a volumetric flow rate of between 0.5 and 5 $h^{-1}$.

10. The process according to claim 9, in which the temperature is between 320° C. and 380° C.

11. The process according to claim 9, in which the pressure is between 0.15 and 0.3 MPa.

12. The process according to claim 9, in which the volumetric flow rate is between 1 and 4 $h^{-1}$.

* * * * *